(12) United States Patent
Heuft et al.

(10) Patent No.: US 8,080,351 B2
(45) Date of Patent: Dec. 20, 2011

(54) TRIARYLMETHANES AND PROCESSES FOR MAKING THE SAME

(75) Inventors: Matthew A. Heuft, Oakville (CA); Alan E. J. Toth, Burlington (CA); Nan-Xing Hu, Oakville (CA); Marko Saban, Etobicoke (CA)

(73) Assignee: Xerox Corporation, Norwalk, CT (US)

( * ) Notice: Subject to any disclaimer, the term of this patent is extended or adjusted under 35 U.S.C. 154(b) by 870 days.

(21) Appl. No.: 12/131,796

(22) Filed: Jun. 2, 2008

(65) Prior Publication Data

US 2009/0297960 A1 Dec. 3, 2009

(51) Int. Cl.
*G03G 5/00* (2006.01)

(52) U.S. Cl. .............................. 430/66; 430/132; 564/315

(58) Field of Classification Search .................... 430/66, 430/132; 564/315
See application file for complete search history.

(56) References Cited

U.S. PATENT DOCUMENTS

| | | |
|---|---|---|
| 3,121,006 A | 2/1964 | Middleton et al. |
| 4,265,990 A | 5/1981 | Stolka et al. |
| 5,709,974 A | 1/1998 | Yuh et al. |
| 5,891,594 A | 4/1999 | Yuh et al. |

OTHER PUBLICATIONS

Tetrahedron Letters, "A simple TiCl4 promoted arylation of orthoformate and benzyl ethers by N, N-dialkylarylamines", Periasamy et al., vol. 48, No. 11, Feb. 15, 2007, pp. 1955-1958.
Journal of Medicinal Chemistry, American Chemical Society, "Synthesis and antitumor activity of tropolone derivatives. 6. Structure-activity relationships of antitumor-active tropolone and 8-hydroxyquinoline derivatives", Yamato M et al., vol. 30, No. 10, Oct. 1, 1987, pp. 1897-1900.
J. Med. Chem., Synthesis and Antitumor Activity of Tropolone Derivatives. , M. Yamato et al., vol. 28, 1985, p. 1026-1031.
ACS Symposium Series: Clean Solvents: Alternative Media for Chemical Reactions and Processing, "Reusable Reaction Systems Derived from Fluorous Solvents or Ionic Liquids and Catalysts", Tomoya Kitazume, vol. 819, 2002, pp. 50-63.
International Search Report, EP Patent Application No. 09160192.2 dated Aug. 24, 2009, 7 pages.

*Primary Examiner* — Mark Chapman
(74) *Attorney, Agent, or Firm* — Pillsbury Winthrop Shaw Pittman LLP

(57) ABSTRACT

Triarylmethane compounds used as antioxidants in overcoat layers to alleviate printing defects and an improved chemical process for the synthesis of these triarylmethane compounds using an acetal derivative of an aldehyde which significantly reduces reaction time and results with the formation of substantially no byproducts.

23 Claims, 1 Drawing Sheet

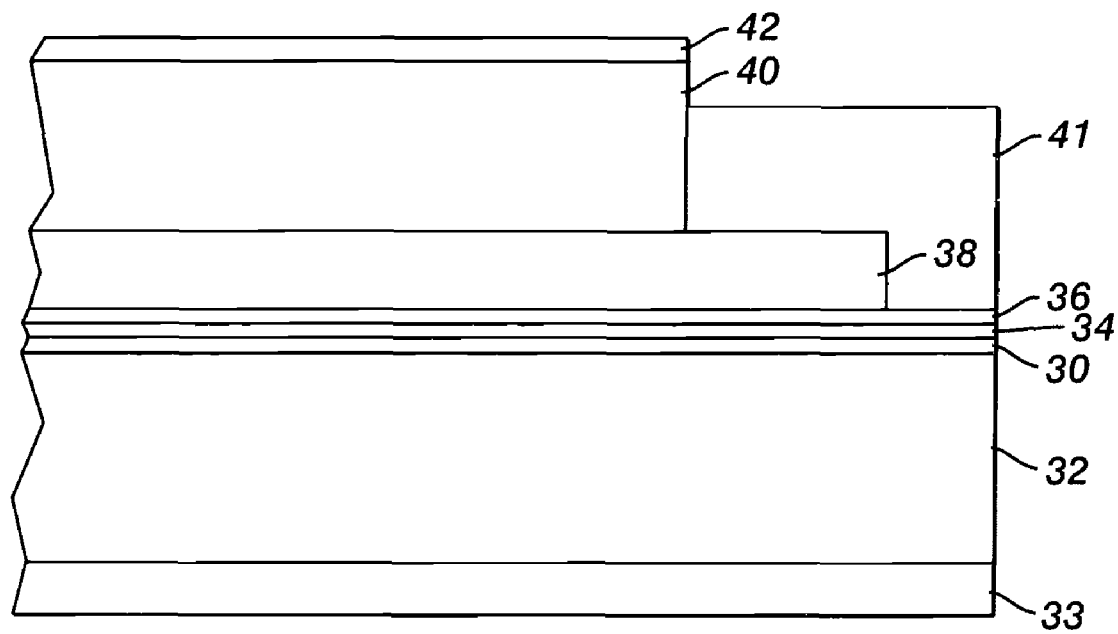

US 8,080,351 B2

TRIARYLMETHANES AND PROCESSES FOR MAKING THE SAME

TECHNICAL FIELD

The present disclosure relates generally to compounds useful as antioxidants incorporated into imaging members, such as layered photoreceptor devices, and improved chemical processes for making the same. The imaging members can be used in electrophotographic, electrostatographic, xerographic and like devices, including printers, copiers, scanners, facsimiles, and including digital, image-on-image, and like devices. More particularly, the embodiments pertain to triarylmethanes used as antioxidants in overcoat layers to alleviate C zone banding and an improved chemical process for the synthesis of these triarylmethane compounds using an acetal derivative of an aldehyde which significantly reduces reaction time and results with the formation of substantially no byproducts.

BACKGROUND

In electrophotography, also known as xerography, electrophotographic imaging or electrostatographic imaging, the surface of an electrophotographic plate, drum, belt or the like (imaging member or photoreceptor) containing a photoconductive insulating layer on a conductive layer is first uniformly electrostatically charged. The imaging member is then exposed to a pattern of activating electromagnetic radiation, such as light. Charge generated by the photoactive pigment move under the force of the applied field. The movement of the charge through the photoreceptor selectively dissipates the charge on the illuminated areas of the photoconductive insulating layer while leaving behind an electrostatic latent image. This electrostatic latent image may then be developed to form a visible image by depositing oppositely charged particles on the surface of the photoconductive insulating layer. The resulting visible image may then be transferred from the imaging member directly or indirectly (such as by a transfer or other member) to a print substrate, such as transparency or paper. The imaging process may be repeated many times with reusable imaging members.

An electrophotographic imaging member may take one of many different forms. For example, layered photoresponsive imaging members are known in the art. U.S. Pat. No. 4,265,990, which is incorporated herein by reference in its entirety, describes a layered photoreceptor having separate photogenerating and charge transport layers. The photogenerating layer is capable of photogenerating holes and injecting the photogenerated holes into the charge transport layer. Thus, in photoreceptors of this type, the photogenerating material generates electrons and holes when subjected to light.

More advanced photoconductive receptors contain highly specialized component layers. For example, a multilayered photoreceptor that can be employed in electrophotographic imaging systems can include one or more of a substrate, an undercoating layer, an optional hole or charge blocking layer, a charge generating layer (including photogenerating material in a binder, e.g., photoactive pigment) over the undercoating and/or blocking layer, and a charge transport layer (including charge transport material in a binder). Additional layers such as an overcoat layer or anticurl back coating layers can also be included. See, for example, U.S. Pat. Nos. 5,891,594 and 5,709,974, which are incorporated herein by reference in their entirety. The term "photoreceptor" is generally used interchangeably with the term "imaging member."

The photogenerating layer utilized in multilayered photoreceptors can include, for example, inorganic photoconductive particles or organic photoconductive particles dispersed in a film forming polymeric binder. Inorganic or organic photoconductive material may be formed as a continuous, homogeneous photogenerating layer.

Upon exposure to light, the charge generated is moved through the photoreceptor. The charge movement is facilitated by the charge transport layer. The speed with which the charge is moved through the charge transport layer directly affects how fast the machine can operate. To achieve the desired increase in machine speed (ppm), the ability of the photoreceptor to move charge must also be increased. Thus, enhancement of charge transport across these layers provides better photoreceptor performance.

Photoreceptor overcoat layers may be formed over the charge transport layer to provide protection against abrasion and wear. Various additives may be incorporated into the overcoat layer to improve performance and further improve protection of the imaging layer as advancement in electrophotographic copiers, duplicators and printers subject the photoreceptor to more stringent requirements and narrow operating limits. Thus, photoreceptor materials are required to exhibit efficient charge generation and charge transport properties, and structural integrity and robustness so as to withstand mechanical abrasion during image development cycles. As such, there is a continued need for improved processes for efficiently synthesizing these photoreceptor materials.

BRIEF SUMMARY

According to embodiments illustrated herein, there is provided an antioxidant for use in photoreceptor layers and improved chemical processes for making the same that address the needs discussed above.

An embodiment may include a process for forming a triarylmethane compound, comprising (a) providing an arylacetal with an electron-rich aryl compound in a reaction mixture, (b) adding a acid catalyst to the reaction mixture, and (c) reacting the arylacetal with the electron-rich aryl compound in the presence of the acid catalyst to produce the triarylmethane compound. In one embodiment, there is provided a triarylmethane obtained by the above-described process. In another embodiment, there is provided an imaging member comprising a substrate, an undercoat layer disposed on the substrate, a charge generating layer disposed on the undercoat layer, a charge transport layer disposed on the charge generating layer, and an overcoat layer disposed on the charge transport layer, the overcoat layer comprising a triarylmethane compound obtained by the process above.

A process for forming a triarylmethane compound, comprising: (a) providing benzaldehyde dimethylacetal with 2-(N-ethyl-m-toluidino)-ethanol in a reaction mixture, (b) adding methane sulfonic acid to the reaction mixture, and (c) reacting the benzaldehyde dimethylacetal with the 2-(N-ethyl-m-toluidino)-ethanol in the presence of the methane sulfonic acid to produce bis-[2-methyl-4-(N-2-hydroxyethyl-N-ethyl-aminophenyl)]-phenylmethane.

A process for forming a triarylmethane compound, comprising: (a) providing benzaldehyde dimethylacetal with N,N-diethyl-3-methyltoludine in a reaction mixture, (b) adding methane sulfonic acid to the reaction mixture, and (c) reacting the benzaldehyde dimethylacetal with the N,N-diethyl-3-methyl-toluidine in the presence of the methane sulfonic acid to produce bis-[2-methyl-4-(N,N-diethylaminophenyl)]-phenylmethane.

BRIEF DESCRIPTION OF THE DRAWINGS

For a better understanding of the present embodiments, reference may be had to the accompanying FIGURE.

The FIGURE is a cross-sectional view of a multilayered electrophotographic imaging member according to an embodiment of the present disclosure.

DETAILED DESCRIPTION

It is understood that other embodiments may be utilized and structural and operational changes may be made without departure from the scope of the embodiments disclosed herein.

The present embodiments relate to triarylmethane compounds useful in overcoat layers for use with imaging members, such as layered photoreceptor devices. The triarylmethanes are used as antioxidants to maintain photoreceptor performance. The photoreceptor area located under the scorotron charging unit tends to print an undesirable black patch during an environmental change-over from A zone (28° C., 85% Relative Humidity (RH)) to C zone (10° C., 15% RH). This occurrence is known as "C zone banding."

Triarylmethanes, such as bis-[2-methyl-4-(N-2-hydroxyethyl-N-ethyl-aminophenyl)]-phenylmethane (DHTPM), bis (4-diethylamino-2-methylphenyl)phenylmethane (BDE-TPM), and bis(4-diethylamino-2-methylphenyl)-4-diethylaminophenylmethane (TrisTPM), have been conventionally synthesized by an acid catalyzed condensation of an arylaldehyde with an excess of an electron-rich aryl compound which involves long reaction times and a difficult purification step. Moreover, the reaction was incomplete and resulted in a low yield of triarylmethane. For example, DHTPM, which is generally selected as a main antioxidant candidate due to its improved performance over other triarylmethanes, is generally synthesized by an acid catalyzed condensation of benzaldehyde with 2-(N-ethyl-m-toluidino)-ethanol in the presence of sulfuric acid and methane sulfonic acid.

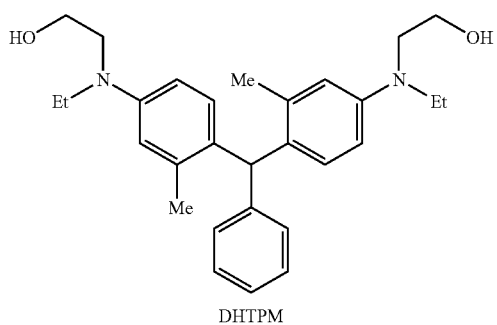

DHTPM

The synthesis involves a reaction time of over 18 hours, azeotropic removal of water and the need for purification due to an excess of the starting material, 2-(N-ethyl-m-toluidino)-ethanol. This synthesis was tested and found to be incomplete after 18 hours as benzaldehyde was detected by high performance liquid chromatography (HPLC). The synthesis provided a yield of only about 67%.

The present embodiments, provide an improved process for synthesizing triarylmethanes by using an acetal derivative of the conventionally used aldehyde, in which the reaction time is reduced significantly from over 18 hours to less than 12 hours with the formation of substantially no aryl-type byproducts. In addition, the acetal derivative may be prepared in situ prior to the synthesis reaction if necessary.

It has been discovered that the use of an arylacetal in place of the arylaldehyde leads to a significant reduction in reaction time. This can be attributed to the easier elimination of an alcohol or diol than water from both a chemical intermediate formed during the reaction and the reaction mixture. The process substantially removes volatile reaction components and/or byproducts during the reacting step. For example, such volatile reaction components and/or byproducts may include methanol, ethanol, isopropanol, n-propanol, n-butanol, and mixtures thereof.

For example, in producing DHTPM, the use of benzaldehyde dimethylacetal instead of benzaldehyde, leads to a significant reduction in reaction time of synthesizing the triarylmethane. In embodiments, the reaction time is reduced by from about 1 hours to about 24 hours. The synthesis reaction of DHTPM using an acetal is illustrated below:

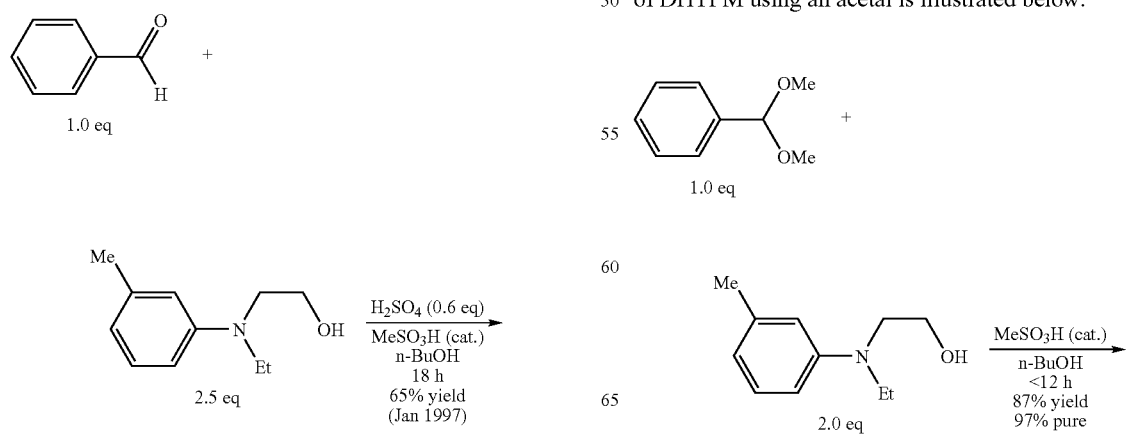

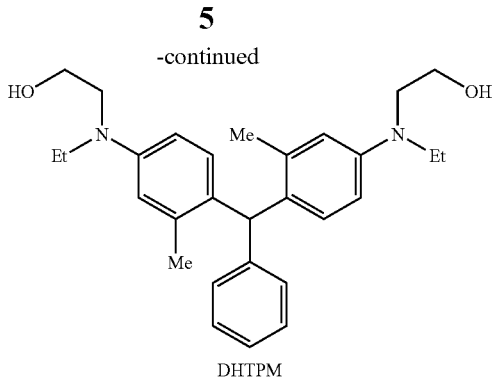

DHTPM

In the above reaction, the amount of 2-(N-ethyl-m-toluidino)-ethanol is reduced by about 0.5 eq which leads to easier purification of the resulting product. In the reaction, a molar ratio of the arylacetal to the electron-rich aryl compound is from about 1:2 to about 1:5. In one embodiment, the arylacetal is selected from the group consisting of $ArCHR_1R_2$ wherein: Ar=an aryl selected from the group consisting of phenyl, napthyl, stilbenyl, biphenyl, anthyl, thienyl, carbozolyl, quinolyl, pyrenyl, perylenyl, and triphenylenyl either unsubstituted or substituted by one or multiple substituents selected from the group consisting of halogen, hydroxy, alkoxy, acyloxy, carboxy, alkoxycarbonyl, cyano, alkyl, cycloalkyl phenyl, napthyl, amino, nitro and sulfo, and mixtures thereof; $R_1$ and $R_2$=$C_1$ to $C_6$ alkoxy and $C_1$ to $C_6$ ω-hydroxyalkoxy, wherein $R_1$ and $R_2$ can be the same or different, and wherein $R_1$ and $R_2$ are joined in a 5- or 6-membered ring (1,3-dioxolane or 1,3-dioxane respectively). In particular embodiments, the arylacetal may be selected from the group consisting of benzaldehyde dimethylacetal, benzaldehyde diethylacetal, benazldehyde di-n-propylacetal, benzaldehyde di-i-propylacetal, and mixtures thereof. The electron-rich aryl compound may be selected from one of the following:

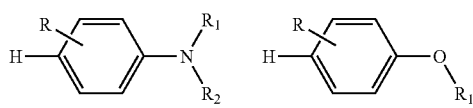

wherein R═H or substituted by one or multiple substituents selected from the group consisting of hydroxy, alkoxy, acyloxy, carboxy, alkoxycarbonyl, cyano, alkyl, cycloalkyl phenyl, napthyl, nitro and sulfo, and mixtures thereof; and $R_1$ and $R_2$═H, alkyl ($C_1$-$C_6$), alkyl ethers, arylalkyl, ω-hydroxyalkyl, ω-aminoalkyl substituents, and mixtures thereof. For example, the electron-rich aryl compound may be selected from the group consisting of 2-(N-ethyl-m-toluidino)-ethanol, N,N-diethyl-3-methyltoluidine, and mixtures thereof. In embodiments, the 2-(N-ethyl-m-toluidino)-ethanol may have flexible substituents on the nitrogen, and be up to 10 carbons. Further suitable aryl compounds include, but are not limited to, para-substituted aryls, arylalkyl, alkylaryl, aryl compounds having functional groups on the end, such as —OH, NH2, NHR with R being up to 6 carbons, and the like. R can be aryl under same conditions, e.g., para substituted, and can be SH, ammonium, cyano, and can have hetero atoms, including oxygen, nitrogen, sulfur, silicon, phosphorus, boron, and the like hydroxy groups, amine groups, ammonium groups, cyano groups, pyridine groups, pyridinium groups, ether groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, azide groups, azo groups, cyanato groups, carboxylate groups, carboxylic acid groups, urethane groups, urea groups, and the like, and mixtures thereof, wherein two or more substituents can be joined together to form a ring. In embodiments, the arylacetal is reacted with an excess of the electron-rich aryl compound in the presence of an acid catalyst. In the reaction the acid has a pKa around two or less (measured in $H_2O$). In embodiments, the temperature of the reacting step is from around 50 to 150° C.

In another embodiment, the acetal can be formed in situ if, for example, the acetal is not commercially available. For example, by treating benzaldehyde with triethylorthoformate and a catalytic amount of methane sulfonic acid, benzaldehyde diethylacetate is formed. Subsequent addition of 2-(N-ethyl-m-toluidino)-ethanol then leads to the formation of DHTPM, as illustrated below:

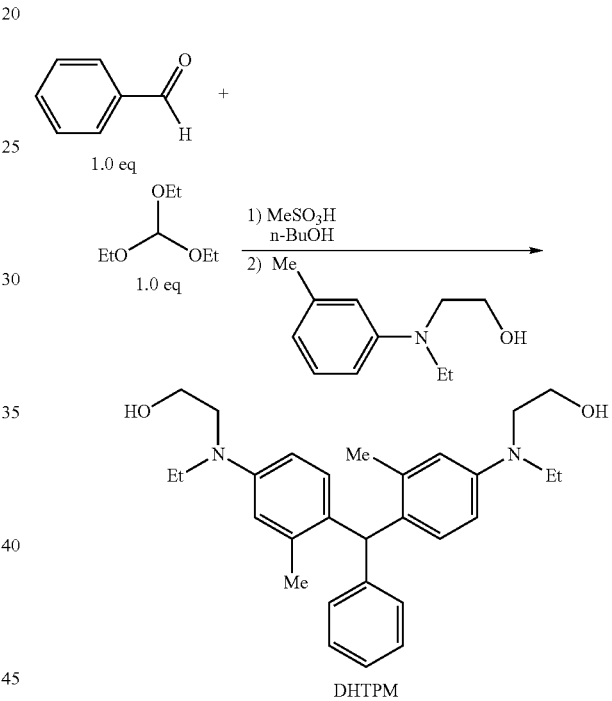

DHTPM

In the in situ reaction, a starting amount of the arylaldehyde to starting amount of the orthoformate may have a molar ratio of from about 1:1 to about 1:10. The orthoformate may be an trialkylorthoformate wherein the alkyl has $C_1$-$C_6$. In a specific embodiment, the orthoformate is triethylorthoformate and the like. The acid catalyst can be selected from the group consisting of methanesulfonic acid, p-toluenesulfonic acid, hydrochloric acid, sulfuric acid, phosphoric acid, trifluoroacetic acid, and the like, and mixtures thereof. The acid catalyst can be the same as or different from the acid catalyst used for reacting the arylacetal and the electron-rich aryl compound in the subsequent formation of the triarylmethane. The arylaldehyde may be ArCHO, where Ar=an aryl selected from the group consisting of phenyl, napthyl, stilbenyl, biphenyl, anthyl, thienyl, carbozolyl, quinolyl, pyrenyl, perylenyl, and triphenylenyl either unsubstituted or substituted by one or multiple substituents selected from the group consisting of halogen, hydroxy, alkoxy, acyloxy, carboxy, alkoxycarbonyl, cyano, alkyl, cycloalkyl phenyl, napthyl, amino, nitro and sulfo, and mixtures thereof.

In another embodiment, the in situ reaction may be between the arylaldehyde and an alcohol in the presence of an acid catalyst. A molar ratio of the arylaldehyde to the alcohol in the reaction mixture may be from about 1:2 to about 1:50.

In the preparation of a related triarylmethane, Tris-TPM, triethylorthoformate was added as a dehydrating agent and the reaction time was noted to be significantly reduced. Triethylorthoformate can act as an in situ drying agent and is believed to be the reason for the significant rate enhancement of the reaction.

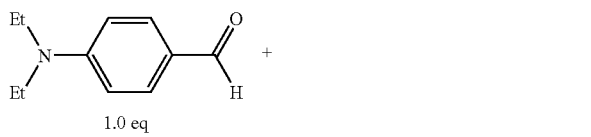

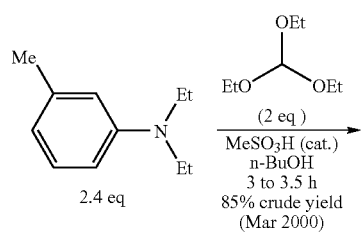

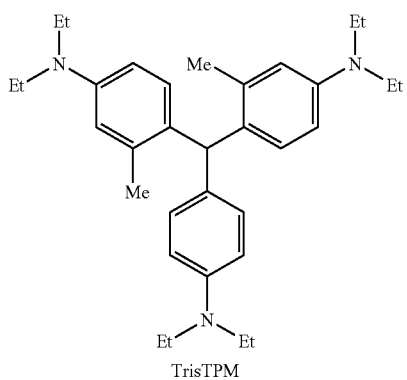

When triethylorthoformate was added to the DHTPM reaction based on benzaldehyde, the reaction time decreased significantly. However, an impurity was detected by HPLC that was not previously formed.

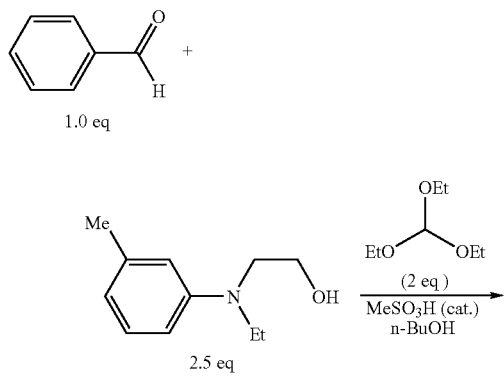

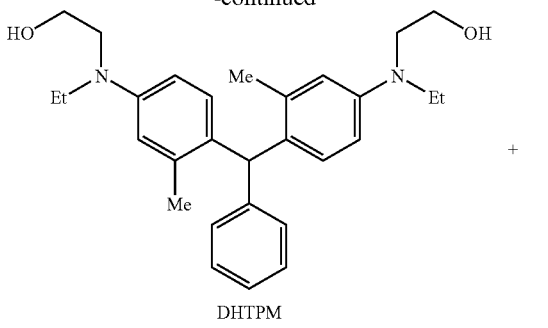

DHTPM impurity (~15%)

This impurity was present in the end yield in an amount of about 15%. The UV-Vis spectra of the impurity and DHTPM are similar, suggesting that 2-(N-ethyl-m-toluidino)-ethanol reacts competitively with triethylorthoformate, although this has yet to be experimentally confirmed. It was noted that HPLC analysis of a sample taken 15 minutes after the reaction had reached 100° C. had no detectable amount of benzaldehyde present.

Orthoformates are known to react with aldehydes to form acetals under acidic conditions. As a control experiment, benzaldehyde was reacted with triethylorthoformate and an acid catalyst prior to addition of 2-(N-ethyl-m-toluidino)-ethanol, and DHTPM was formed with no impurity detected. Thus, it was discovered that the acetal can be formed in situ, for example in the case of benzaldehyde diethylacetate, by treating benzaldehyde with triethylorthoformate and a catalytic amount of methane sulfonic acid. Subsequent addition of 2-(N-ethyl-m-toluidino)-ethanol then leads to the formation of DHTPM.

According to further embodiments herein, an electrophotographic imaging member is provided, which generally comprises at least a substrate layer, an imaging layer disposed on the substrate, and an optional overcoat layer disposed on the imaging layer. The imaging member includes, as imaging layers, a charge transport layer and a charge generating layer. The imaging member can be employed in the imaging process of electrophotography, where the surface of an electrophotographic plate, drum, belt or the like (imaging member or photoreceptor) containing a photoconductive insulating layer on a conductive layer is first uniformly electrostatically charged. The imaging member is then exposed to a pattern of activating electromagnetic radiation, such as light. The radiation selectively dissipates the charge on the illuminated areas of the photoconductive insulating layer while leaving behind an electrostatic latent image. This electrostatic latent image may then be developed to form a visible image by depositing oppositely charged particles on the surface of the photoconductive insulating layer. The resulting visible image may then be transferred from the imaging member directly or indirectly (such as by a transfer or other member) to a print substrate, such as transparency or paper. The imaging process may be repeated many times with reusable imaging members.

In a typical electrostatographic reproducing apparatus such as electrophotographic imaging system using a photoreceptor, a light image of an original to be copied is recorded in the form of an electrostatic latent image upon an imaging member and the latent image is subsequently rendered visible by the application of a developer mixture. The developer, having toner particles contained therein, is brought into contact with the electrostatic latent image to develop the image on an electrostatographic imaging member which has a chargeretentive surface. The developed toner image can then be transferred to a copy substrate, such as paper, that receives the image via a transfer member.

Alternatively, the developed image can be transferred to another intermediate transfer device, such as a belt or a drum, via the transfer member. The image can then be transferred to the paper by another transfer member. The toner particles may be transfixed or fused by heat and/or pressure to the paper. The final receiving medium is not limited to paper. It can be various substrates such as cloth, conducting or non-conducting sheets of polymer or metals. It can be in various forms, sheets or curved surfaces. After the toner has been transferred to the imaging member, it can then be transfixed by high pressure rollers or fusing component under heat and/or pressure.

An embodiment of an imaging member is illustrated in FIG. 1. The substrate 32 has an optional electrical conductive layer 30. An optional undercoat layer 34 can also be applied over the conductive layer, as well as an optional adhesive layer 36 over the undercoat layer 34. The charge generating layer 38 is illustrated between an adhesive layer 36 and a charge transport layer 40. An optional ground strip layer 41 operatively connects the charge generating layer 38 and the charge transport layer 40 to the conductive layer 30. An anticurl back coating layer 33 may be applied to the side of the substrate 32 opposite from the electrically active layers to render desired imaging member flatness. Other layers of the imaging member may also include, for example, an optional overcoat layer 42 directly over the charge transport layer 40 to provide protection against abrasion and wear.

The conductive ground plane 30 over the substrate 32 is typically a thin, metallic layer, for example a 10 nanometer thick titanium coating, which may be deposited over the substrate by vacuum deposition or sputtering processes. The layers 34, 36, 38, 40 and 42 may be separately and sequentially deposited onto the surface of the conductive ground plane 30 of substrate 32 as wet coating layers of solutions comprising one or more solvents, with each layer being completely dried before deposition of the subsequent coating layer. The anticurl back coating layer 33 may also be solution coated, but is applied to the back side of substrate 32, to balance the curl and render imaging member flashes.

Illustrated herein are embodiments of an imaging member comprising a substrate, a charge generating layer disposed on the substrate, and at least one charge transport layer disposed on the charge generating layer. An overcoat layer is disposed over the charge transport layer to provide protection to the imaging layers. The overcoat layer comprises a triarylmethane compound for use as an antioxidant. The triarylmethane compound is obtained by reacting an arylacetal with an electron-rich aryl compound, which provides a substantially complete reaction in much less time than convention syntheses. In further embodiments, the triarylmethane incorporated in the overcoat layer is DHTPM obtained by reacting benzaldehyde dimethylacetal with 2-(N-ethyl-m-toluidino)-ethanol. Other embodiments include overcoat layers incorporating BDTPM and TrisTPM obtained through similar synthesis and used as overcoat layer antioxidants.

In further embodiments, the overcoat layer may comprise a triarylmethane compound which is obtained by first synthesizing an arylacetal through reaction of an arylaldehyde with an orthoformate in the presence of an acid catalyst and subsequently adding an electron-rich aryl compound, such as 2-(N-ethyl-m-toluidino)-ethanol.

The overcoat layers may comprise a dispersion of nanoparticles, such as silica, metal oxides, ACUMIST (waxy polyethylene particles), polytetrafluoroethylene (PTFE), and the like. The nanoparticles may be used to enhance the lubricity, scratch resistance, and wear resistance of the charge transport layer.

Any suitable and conventional technique may be utilized to form and thereafter apply the overcoat layer mixture to the imaging layer. Typical application techniques include, for example extrusion coating, draw bar coating, roll coating, wire wound rod coating, and the like. The overcoat layer may be formed in a single coating step or in multiple coating steps. Drying of the deposited coating may be effected by any suitable conventional technique such as oven drying, infra red radiation drying, air drying and the like. The thickness of the dried overcoat layer may depend upon the abrasiveness of the charging, cleaning, development, transfer, etc. system employed and can range up to about 15 microns. In these embodiments, the thickness can be from about 3 microns and about 10 microns in thickness. A description of the other layers of the imaging member is provided as follows.

Illustrative examples of substrate layers selected for the imaging members may be opaque or substantially transparent, and may comprise any suitable material having the requisite mechanical properties. Thus, the substrate may comprise a layer of insulating material including inorganic or organic polymeric materials, such as MYLAR a commercially available polymer, MYLAR-containing titanium, a layer of an organic or inorganic material having a semiconductive surface layer, such as indium tin oxide, or aluminum arranged thereon, or a conductive material inclusive of aluminum, aluminized polyethylene terephthalate, titanized polyethylene chromium, nickel, brass or the like. The substrate may be flexible, seamless, or rigid, and may have a number of many different configurations, such as for example a plate, a cylindrical drum, a scroll, an endless flexible belt, and the like. In one embodiment, the substrate is in the form of a seamless flexible belt. The anticurl back coating is applied to the back of the substrate.

The thickness of the substrate layer depends on many factors, including economical considerations, thus this layer may be of substantial thickness, for example over 3,000 microns, or of minimum thickness providing there are no significant adverse effects on the member. In embodiments, the thickness of this layer is from about 75 microns to about 300 microns.

Moreover, the substrate may contain thereover an undercoat layer in some embodiments, including known undercoat layers, such as suitable phenolic resins, phenolic compounds, mixtures of phenolic resins and phenolic compounds, titanium oxide, silicon oxide mixtures like $TiO_2/SiO_2$.

In embodiments, the undercoat layer may also contain a binder component. Examples of the binder component include, but are not limited to, polyamides, vinyl chlorides, vinyl acetates, phenolic resins, polyurethanes, aminoplasts, melamine resins, benzoguanamine resins, polyimides, polyethylenes, polypropylenes, polycarbonates, polystyrenes, acrylics, styrene acrylic copolymers, methacrylics, vinylidene chlorides, polyvinyl acetals, epoxys, silicones, vinyl chloride-vinyl acetate copolymers, polyvinyl alcohols, polyesters, polyvinyl butyrals, nitrocelluloses, ethyl celluloses, caseins, gelatins, polyglutamic acids, starches, starch acetates, amino starches, polyacrylic acids, polyacrylamides, zirconium chelate compounds, titanyl chelate compounds, titanyl alkoxide compounds, organic titanyl compounds, silane coupling agents, and combinations thereof. In embodiments, the binder component comprises a member selected from the group consisting of phenolic-formaldehyde resin, melamine-formaldehyde resin, urea-formaldehyde resin, benzoguanamine-formaldehyde resin, glycoluril-formaldehyde resin, acrylic resin, styrene acrylic copolymer, and mixtures thereof.

In embodiments, the undercoat layer may contain an optional light scattering particle. In various embodiments, the light scattering particle has a refractive index different from the binder and has a number average particle size greater than about 0.8 μm. In various embodiments, the light scattering particle is amorphous silica P-100 commercially available from Espirit Chemical Co. In various embodiments, the light scattering particle is present in an amount of about 0% to about 10% by weight of a total weight of the undercoat layer.

In embodiments, the undercoat layer may contain various colorants. In various embodiments, the undercoat layer may contain organic pigments and organic dyes, including, but not limited to, azo pigments, quinoline pigments, perylene pigments, indigo pigments, thioindigo pigments, bisbenzimidazole pigments, phthalocyanine pigments, quinacridone pigments, quinoline pigments, lake pigments, azo lake pigments, anthraquinone pigments, oxazine pigments, dioxazine pigments, triphenylmethane pigments, azulenium dyes, squalium dyes, pyrylium dyes, triallylmethane dyes, xanthene dyes, thiazine dyes, and cyanine dyes. In various embodiments, the undercoat layer may include inorganic materials, such as amorphous silicon, amorphous selenium, tellurium, a selenium-tellurium alloy, cadmium sulfide, antimony sulfide, titanium oxide, tin oxide, zinc oxide, and zinc sulfide, and combinations thereof. In embodiments, the thickness of the undercoat layer may be from about 0.1 μm to 30 μm.

A photoconductive imaging member herein can comprise in embodiments in sequence of a supporting substrate, an undercoat layer, an adhesive layer, a charge generating layer and a charge transport layer. For example, the adhesive layer can comprise a polyester with, for example, an $M_w$ of about 75,000, and an $M_n$ of about 40,000.

In embodiments, a photoconductive imaging member further includes an adhesive layer of a polyester with an $M_w$ of about 70,000, and an $M_n$ of about 35,000. The adhesive layer may comprise any suitable material, for example, any suitable film forming polymer. Typical adhesive layer materials include for example, but are not limited to, copolyester resins, polyarylates, polyurethanes, blends of resins, and the like. Any suitable solvent may be selected in embodiments to form an adhesive layer coating solution. Typical solvents include, but are not limited to, for example, tetrahydrofuran, toluene, hexane, cyclohexane, cyclohexanone, methylene chloride, 1,1,2-trichloroethane, monochlorobenzene, and mixtures thereof, and the like.

Generally, the thickness of the charge generating layer depends on a number of factors, including the thicknesses of the other layers and the amount of photogenerator material or pigment contained in the charge generating layers. Accordingly, this layer can be of a thickness of, for example, from about 0.05 micron to about 5 microns, or from about 0.25 micron to about 2 microns when, for example, the pigments are present in an amount of from about 30 to about 75 percent by volume. The maximum thickness of this layer in embodiments is dependent primarily upon factors, such as photosensitivity, electrical properties and mechanical considerations. The charge generating layer binder resin present in various suitable amounts, for example from about 1 to about 50 or from about 1 to about 10 weight percent, may be selected from a number of known polymers, such as poly(vinyl butyral), poly(vinyl carbazole), polyesters, polycarbonates, poly(vinyl chloride), polyacrylates and methacrylates, copolymers of vinyl chloride and vinyl acetate, phenoxy resins, polyurethanes, poly(vinyl alcohol), polyacrylonitrile, polystyrene, and the like.

In embodiments, the charge transport layer includes a charge transport component and a binder. The charge transport layer may be between about 10 μm and about 50 μm in thickness. Examples of the binder materials selected for the charge transport layers include components, such as those described in U.S. Pat. No. 3,121,006, the disclosure of which is totally incorporated herein by reference. Specific examples of polymer binder materials include polycarbonates, polyarylates, acrylate polymers, vinyl polymers, cellulose polymers, polyesters, polysiloxanes, polyamides, polyurethanes, poly (cyclo olefins), and epoxies, and random or alternating copolymers thereof. In embodiments electrically inactive binders are comprised of polycarbonate resins with for example a molecular weight of from about 20,000 to about 100,000 and more specifically with a molecular weight $M_w$ of from about 50,000 to about 100,000. Examples of polycarbonates are poly(4,4'-isopropylidene-diphenylene)carbonate (also referred to as bisphenol-A-polycarbonate, poly(4,4'-cyclohexylidinediphenylene)carbonate (referred to as bisphenol-Z polycarbonate), poly(4,4'-isopropylidene-3,3'-dimethyl-diphenyl)carbonate (also referred to as bisphenol-C-polycarbonate) and the like. In embodiments, the charge transport layer, such as a hole transport layer, may have a thickness from about 10 to about 55 microns. In embodiments, electrically inactive binders are selected comprised of polycarbonate resins having a molecular weight of from about 20,000 to about 100,000 or from about 50,000 to about 100,000. Generally, the transport layer contains from about 10 to about 75 percent by weight of the charge transport material or from about 35 percent to about 50 percent of this material.

In embodiments, the at least one charge transport layer comprises from about 1 to about 7 layers. For example, in embodiments, the at least one charge transport layer comprises a top charge transport layer and a bottom charge transport layer, wherein the bottom layer is situated between the charge generating layer and the top layer.

Various exemplary embodiments encompassed herein include a method of imaging which includes generating an electrostatic latent image on an imaging member, developing a latent image, and transferring the developed electrostatic image to a suitable substrate.

While the description above refers to particular embodiments, it will be understood that many modifications may be made without departing from the spirit thereof. The accompanying claims are intended to cover such modifications as would fall within the true scope and spirit of embodiments herein.

The presently disclosed embodiments are, therefore, to be considered in all respects as illustrative and not restrictive, the scope of embodiments being indicated by the appended claims rather than the foregoing description. All changes that come within the meaning of and range of equivalency of the claims are intended to be embraced therein.

EXAMPLES

The examples set forth herein below and are illustrative of different compositions and conditions that can be used in practicing the present embodiments. All proportions are by weight unless otherwise indicated. It will be apparent, however, that the present embodiments can be practiced with many types of compositions and can have many different uses in accordance with the disclosure above and as pointed out hereinafter.

Example 1

2-(N-ethyl-m-toluidino)-ethanol (108 g, 106 mL, 600 mmol, 2.0 eq), n-butanol (105 mL), benzaldehyde dimethyl acetal (45 mL, 300 mmol, 1 eq), and methane sulfonic acid (3.9 mL, 60 mmol, 0.2 eq) were combined in a 500 mL RBF equipped with magnetic stirring, Dean-Stark apparatus and a reflux condenser. The reaction mixture was a pale-yellow color.

The mixture was heated in an oil bath (temperature=120° C.) and MeOH was collected in the Dean-Stark trap (11.3 mL). The reaction was complete in less than 12 hours. HPLC analysis gave the following results (12 hours, crude): residual 2-(N-ethyl-m-toluidino)-ethanol (10.4%), product (86%).

The reaction was cooled to room temperature and NaOH (1M aq, 60 mL) was added. The mixture was stirred at room temperature for 20 minutes. $NH_4Cl$ (sat aq, 20 mL) was added (pH between 6 and 7) and the mixture was diluted with EtOAc (400 mL) and transferred to a separatory funnel. The organics were washed with water (2×300 mL) and brine (400 mL), dried ($MgSO_4$), filtered and concentrated to viscous amber oil. The residual BuOH and unreacted starting material was removed by high vacuum distillation (<1 mmHg, 150° C.) to afford an amber glass (117.2 g, 87%). The sample was hot transferred to an aluminum foil tray and solidified to a yellow glass. An off-white powder was obtained after crushing and grinding. The product was characterized by $^1H$ and $^{13}C$ NMR, HPLC, thermal gravometric analysis (TGA), and differential scanning calorimetry (DSC). Sample purity was determined to be about 97% by HPLC.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others. Unless specifically recited in a claim, steps or components of claims should not be implied or imported from the specification or any other claims as to any particular order, number, position, size, shape, angle, color, or material.

All the patents and applications referred to herein are hereby specifically, and totally incorporated herein by reference in their entirety in the instant specification.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A process for forming a triarylmethane compound, comprising:
    (a) providing an arylacetal with an electron-rich aryl compound in a reaction mixture;
    (b) adding an acid catalyst to the reaction mixture; and
    (c) reacting the arylacetal with the electron-rich aryl compound in the presence of the acid catalyst to produce the triarylmethane compound.

2. The process of claim 1, wherein the temperature of the reacting step is from around 50 to 150° C.

3. The process of claim 1, wherein volatile reaction components and/or byproducts are substantially removed during the reacting step.

4. The process of claim 3, wherein the volatile reaction components and/or byproducts substantially removed during the reacting step is selected from the group consisting of methanol, ethanol, isopropanol, n-propanol, n-butanol, and mixtures thereof.

5. The process of claim 1, wherein the arylacetal is selected from the group consisting of $ArCHR_1R_2$ wherein: Ar=an aryl selected from the group consisting of phenyl, napthyl, stilbenyl, biphenyl, anthyl, thienyl, carbozolyl, quinolyl, pyrenyl, perylenyl, and triphenylenyl either unsubstituted or substituted by one or multiple substituents selected from the group consisting of halogen, hydroxy, alkoxy, acyloxy, carboxy, alkoxycarbonyl, cyano, alkyl, cycloalkyl phenyl, napthyl, amino, nitro and sulfo, and mixtures thereof; $R_1$ and $R_2$=$C_1$ to $C_6$ alkoxy and $C_1$ to $C_6$ ω-hydroxyalkoxy, wherein $R_1$ and $R_2$ can be the same or different, and wherein $R_1$ and $R_2$ are joined in a 5- or 6-membered ring (1,3-dioxolane or 1,3-dioxane respectively).

6. The process of claim 5, wherein the arylacetal is selected from the group consisting of benzaldehyde dimethylacetal, benzaldehyde diethylacetal, benzaldehyde di-n-propylacetal, benzaldehyde di-i-propylacetal, and mixtures thereof.

7. The process of claim 1, wherein the electron-rich aryl compound is selected from one of the following:

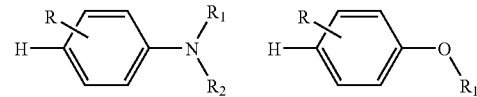

wherein R=H or substituted by one or multiple substituents selected from the group consisting of hydroxy, alkoxy, acyloxy, carboxy, alkoxycarbonyl, cyano, alkyl, cycloalkyl phenyl, napthyl, nitro and sulfo, and mixtures thereof; and $R_1$ and $R_2$=H, alkyl($C_1$-$C_6$), alkyl ethers, arylalkyl, ω-hydroxyalkyl, ω-aminoalkyl substituents, and mixtures thereof.

8. The process of claim 1, wherein the electron-rich aryl compound is selected from the group consisting of 2-(N-ethyl-m-toluidino)-ethanol, N,N-diethyl-3-methyltoluidine, and mixtures thereof.

9. The process of claim 1, wherein a molar ratio of the arylacetal to the electron-rich aryl compound in the reaction mixture is from about 1:2 to about 1:5.

10. The process of claim 1, wherein the acid has a pKa around two or less (measured in $H_2O$).

11. The process of claim 10, wherein the acid is selected from the group consisting of methanesulfonic acid, p-toluenesulfonic acid, hydrochloric acid, sulfuric acid, phosphoric acid, trifluoroacetic acid.

12. The process of claim 1, wherein the arylacetal is obtained by reacting an arylaldehyde with a trialkylorthoformate in the presence of the acid catalyst prior to the addition of the electron-rich aryl compound to the reaction mixture, and wherein the alkyl has $C_1$-$C_6$.

13. The process of claim 12, wherein the arylaldehyde is ArCHO, where Ar=an aryl selected from the group consisting of phenyl, napthyl, stilbenyl, biphenyl, anthyl, thienyl, carbozolyl, quinolyl, pyrenyl, perylenyl, and triphenylenyl either unsubstituted or substituted by one or multiple substituents selected from the group consisting of halogen, hydroxy, alkoxy, acyloxy, carboxy, alkoxycarbonyl, cyano, alkyl, cycloalkyl phenyl, napthyl, amino, nitro and sulfo, and mixtures thereof.

14. The process of claim 12, wherein the arylaldehyde is benzaldehyde.

15. The process of claim 12, wherein a molar ratio of the arylaldehyde to the orthoformate is from about 1:1 to about 1:10.

16. The process of claim 12, wherein the trialkylorthoformate is a $C_1$-$C_6$ alkyl.

17. The process of claim 1, wherein the arylacetal is obtained by reacting an arylaldehyde with an alcohol in the presence of the acid catalyst prior to the addition of the electron-rich aryl compound to the reaction mixture.

18. The process of claim 17, wherein a molar ratio of the arylaldehyde to the alcohol is from about 1:2 to about 1:50.

19. The process of claim 1 having a reaction time that is from about 1 hour to about 24 hours less than that of a process using an arylaldehyde in place of the arylacetal.

20. A triarylmethane obtained by the process of claim 1.

21. An imaging member comprising:
a substrate;
an undercoat layer disposed on the substrate
a charge generating layer disposed on the undercoat layer;
a charge transport layer disposed on the charge generating layer; and
an overcoat layer disposed on the charge transport layer, the overcoat layer comprising a triarylmethane compound obtained by the process of claim 1.

22. A process for forming a triarylmethane compound, comprising:
(a) providing benzaldehyde dimethylacetal with 2-(N-ethyl-m-toluidino)-ethanol in a reaction mixture;
(b) adding methane sulfonic acid to the reaction mixture; and
(c) reacting the benzaldehyde dimethylacetal with the 2-(N-ethyl-m-toluidino)-ethanol in the presence of the methane sulfonic acid to produce bis-[2-methyl-4-(N-2-hydroxyethyl-N-ethylaminophenyl)]-phenylmethane.

23. A process for forming a triarylmethane compound, comprising:
(a) providing benzaldehyde dimethylacetal with N,N-diethyl-3-methyltoludine in a reaction mixture;
(b) adding methane sulfonic acid to the reaction mixture; and
(c) reacting the benzaldehyde dimethylacetal with the N,N-diethyl-3-methyl-toluidine in the presence of the methane sulfonic acid to produce bis-[2-methyl-4-(N,N-diethylaminophenyl)]-phenylmethane.

* * * * *